United States Patent
Marchitto et al.

(10) Patent No.: US 6,689,380 B1
(45) Date of Patent: Feb. 10, 2004

(54) REMOTE AND LOCAL CONTROLLED DELIVERY OF PHARMACEUTICAL COMPOUNDS USING ELECTROMAGNETIC ENERGY

(76) Inventors: Kevin S. Marchitto, 127 Bellbird Road, Mt. Eliza 3930 VIC (AU); Stephen T. Flock, 17 Gillards Road, Mt. Eliza 3930 (AU)

( * ) Notice: Subject to any disclaimer, the term of this patent is extended or adjusted under 35 U.S.C. 154(b) by 0 days.

(21) Appl. No.: 09/573,147

(22) Filed: May 17, 2000

Related U.S. Application Data

(60) Provisional application No. 60/134,486, filed on May 17, 1999.

(51) Int. Cl.[7] ............................. A61F 31/00; A61K 9/70
(52) U.S. Cl. .................... 424/449; 424/448; 424/447; 424/445; 424/443; 424/422; 424/423; 607/88; 607/89; 607/100; 607/101; 600/9; 600/10
(58) Field of Search ................................ 424/422, 443, 424/447, 49, 423; 604/890.1, 19; 600/9, 10; 607/88, 89, 100, 101

(56) References Cited

U.S. PATENT DOCUMENTS

| | | | |
|---|---|---|---|
| 5,028,435 A | * 7/1991 | Katz et al. | 424/484 |
| 5,458,140 A | 10/1995 | Eppstein et al. | 128/632 |
| 5,542,935 A | * 8/1996 | Unger et al. | 604/190 |
| 5,865,744 A | * 2/1999 | Lemelson | 600/407 |
| 6,160,509 A | * 12/2000 | Graziani et al. | 342/357.09 |
| 6,416,471 B1 | * 7/2002 | Kumar et al. | 600/300 |
| 6,542,765 B1 | * 4/2003 | Guy et al. | 600/345 |

* cited by examiner

*Primary Examiner*—Thurman K. Page
*Assistant Examiner*—Liliana Di Nola Baron
(74) *Attorney, Agent, or Firm*—Benjamin Aaron Adler

(57) ABSTRACT

The present invention provides a method/system for remote and local controlled delivery of pharmaceutical compounds or biomolecule collection using electromagnetic energy. Controlled electromagnetic energy driven systems are integrated into patches and other delivery devices. Also provided is a drug delivery or biomolecule collection patch electronically monitored by global positioning system.

11 Claims, 1 Drawing Sheet

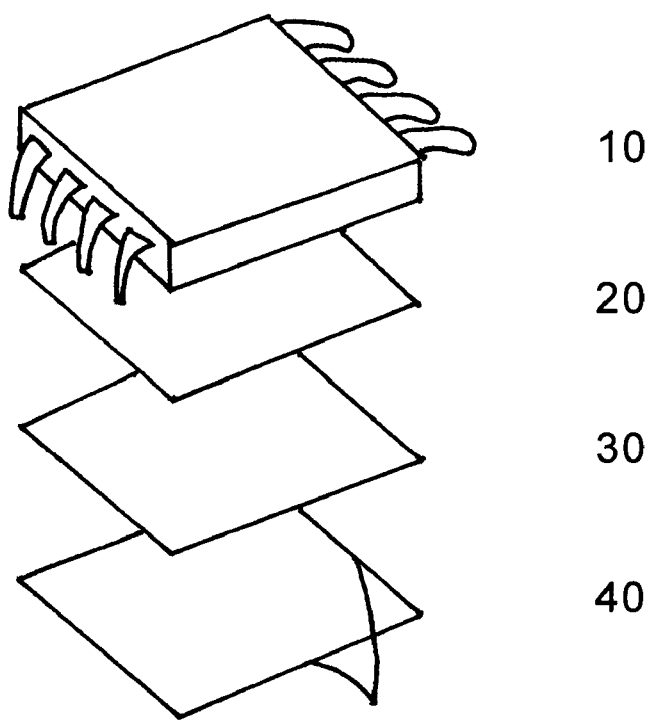

REMOTE AND LOCAL CONTROLLED DELIVERY OF PHARMACEUTICAL COMPOUNDS USING ELECTROMAGNETIC ENERGY

CROSS-REFERENCE TO RELATED APPLICATION

This non-provisional patent application claims benefit of provisional patent application U.S. Serial No. 60/134,486, filed May 17, 1999, now abandoned.

BACKGROUND OF THE INVENTION

1. Field of the Invention

The present invention relates generally to the fields of medical physics and drug delivery. More specifically, the present invention relates to methods and devices for controlling the delivery of pharmaceutical compounds through the skin and other tissue interfaces.

2. Description of the Related Art

Drug delivery is a critical aspect of medical treatment. In many cases, correct administration of drugs is critical to the overall efficacy of its action, and thus, patient compliance becomes a significant factor in therapy. For this reason, the physician should carefully monitor drug delivery.

Drug delivery is particularly important in acute care settings. Patients must often endure long hospital stays post-surgery or other treatment to ensure that drugs are administered properly. In this case, and many others, a patient must remain in close contact with the physician during the course of treatment. This compliance issue, and the cost of long-term hospital stays, has resulted in significant research and development of devices capable of delivering controlled, continuous and sustainable release of therapeutics.

Skin has a very thin layer of dead cells, called the stratum corneum, which acts as an impermeable layer to matter on either side of the layer. The stratum corneum is what primarily provides the skin's barrier function. If the stratum corneum is removed or somehow altered, then materials within the body can more easily diffuse out to the surface of the skin, and materials outside the body can more easily diffuse into the skin. Alternatively, compounds referred to as permeation enhancers (e.g. alcohol) or drug carriers (e.g. liposomes) can be used, with some success, to penetrate the stratum corneum. In any case, the barrier function of the skin presents a very significant problem to pharmaceutical manufacturers who may be interested in topical administration of drugs, or in transcutaneous collection of bodily fluids.

Mucosa, which is the moist lining of many tubular structures and cavities (e.g. nasal sinuses and mouth), consists in part of an epithelial surface layer. This surface layer, which consists of sheets of cells with strong intercellular bonds, in single or multiple layers, and that have a non-keratinized or keratinized epithelium. On the basolateral side of the epithelium is a thin layer of collagen, proteoglycans and glucoproteins called the basal lamina, and which serves to bind the epithelial layer to the adjacent cells or matrix. The mucosa acts as a barrier to prevent the significant absorption of topically applied substances, as well as the desorption of biomolecules and substances from within the body. The degree to which mucosa acts as a barrier, and the exact nature of the materials to which the mucosa is impermeable or permeable, depends on the anatomical location. For example, the epithelium of the bladder is 10,000 times less "leaky" to ions than the intestinal epithelium.

The mucosa is substantially different from skin in many ways. For example, mucosa does not have a stratum corneum. Despite this difference, permeation of compounds across mucosa is limited and somewhat selective. The most recent model of the permeability of mucosa is that the adjacent cells in the epithelium are tightly bound by occluding junctions, which inhibit most small molecules from diffusing through the mucosa, while allowing effusion of mucoid proteins. The molecular structure of the epithelium consists of strands of proteins that link together between the cells, as well as focal protein structures such as desmosomes. The permeation characteristics of mucosa are not fully understood, but it is conceivable that the selective permeability of the mucosa may depend on this epithelial layer, which may or may not be keratinized, as well as the basal lamina. While it has been shown that removal or alteration of the stratum corneum of skin can lead to an increase in skin permeability, there is no corresponding layer on the mucosa to modify. Thus, it is not obvious that electromagnetic energy irradiation will cause a modification of the permeability of mucosa.

Various methods have been used for facilitating the delivery of compounds across the skin and other membranes. Iontophoresis uses an electric current to increase the permeation rate of charged molecules. Iontophoresis however is dependent on charge density of the molecule, and furthermore, has been known to cause burning in patients. Use of ultrasound has also been tested whereby application of ultrasonic energy to the skin results in a transient alteration of the skin, resulting in increased permeability to substances. Electromagnetic energy produced by lasers may be used to ablate stratum corneum in order to make the skin more permeable to pharmaceutical substances (U.S. Pat. No. 4,775,361), and, impulse transients generated by lasers or by mechanical means may be used to make alterations in epithelial layers that result in improved permeation of compounds (U.S. Pat. No. 5,614,502).

There are many therapeutic and diagnostic procedures that would benefit from a transmucosal or transendothelial route of administration or collection. For example, local anesthetics, such as lidocaine, are delivered to a region prior to a medical treatment. Such a local administration of lidocaine could be efficacious at providing anesthesia, but would minimize any side-effects and eliminate the need for a needle. Local administration of an antineoplastic drug into the bladder wall could greatly minimize the time required for a patient to hold a drug in the bladder during chemotherapy.

Electrosurgery, which is a method whereby tissue coagulation and/or dissection can be effected. In electrosurgery, radiofrequency (RF) current is applied to tissue applied by an (active) electrode. In a bipolar system, the current is passed through tissue between two electrodes on the same surgical instrument, such as a forceps. In a monopolar system, a return-path (ground) electrode is affixed in intimate electrical contact, with some part of the patient. Because of the importance of the ground electrode providing the lowest impedance conductive path for the electrical current, protection circuits monitoring the contact of the ground with the patient are often employed whereupon an increase in ground electrode-skin impedance results in the instrument shutting down. Factors involved in electrosurgical system include treatment electrode shape, electrode position (contact or non-contact) with respect to the tissue surface, frequency and modulation of the RF, power of the RF and time for which it is applied to the tissue surface, peak-to-peak voltage of the radiofrequency, and tissue type.

In typical electrosurgical systems, radiofrequency frequencies of 300 kHz to 4 MHz are used since nerve and muscle stimulation cease at frequencies beyond 100 kHz. For example, all else being equal, decreasing electrode size translates into increased current density in the tissue proximal to the electrode and so a more invasive tissue effect, such as dissection, as compared to coagulation. Similarly, all else being equal, if the electrode is held close to the tissue, but not in contact, then the area of RF-tissue interaction is small (as compared to the area when the electrode is in contact with the tissue), and so the effect on the tissue is more invasive. By changing the waveform of the applied RF from a continuous sinusoid to packets of higher peak voltage. sinusoids separated by dead time (i.e. a duty cycle of, say, 6%), then the tissue effect (all else being equal) can be changed from dissection to coagulation. Holding all else equal, increasing the voltage of the waveform increases the invasiveness of the tissue effect. Of course, the longer the tissue is exposed to the radiofrequency, the greater the tissue effect. Finally, different tissues respond to radiofrequency differently because of their different electrical conductive properties, concentration of current. carrying ions, and different thermal properties.

The prior art is deficient in the lack of effective means of controlling the rate of pharmaceutical delivery or biomolecule collection by utilizing electromagnetic energy, wherein controlled electromagnetic energy driven systems are integrated into patches and other delivery devices. The present invention fulfills this long-standing need and desire in the art.

SUMMARY OF THE INVENTION

The present invention provides a microprocessor which may be controlled, and may be communicated with, over analog and digital telecommunication links, including the Internet. Specifically, the present invention describes microprocessor-controlled transdermal patches that use electromagnetic energy to enhance the uptake of a pharmaceutical formulation in contact with a membrane or skin. The devices could also be used to increase the diffusion of the substances, as well as endogenous biomolecules, out of tissue. The electromagnetic energy inherent to the inventions described herein is often referred to as microwave (MW) and radiofrequency (RF).

The application of the present invention is not limited to delivery across oral mucosa or skin. Other anatomical structures including, for example, vaginal, uterine, intestinal, buccal, tongue, nasopharyngeal, anal, and bladder walls, as well as vascular, lymphatic and urethral vessels are also applicable. Importantly, the present invention can be used to breach compromised or intact stratum corneum and the tissue layers underneath in order to deliver compounds across skin, and with many drugs, through intact skin. Furthermore, this method may be used to control systems that drive substances across non-biological membranes and films.

In one embodiment of the present invention, there is provided a method for controlling delivery of a pharmaceutical compound in a subject, comprising the steps of: irradiating the subject with electromagnetic energy; and applying the pharmaceutical compound to the subject, wherein the compound is contained in a patch. Preferably, the electromagnetic energy is selected from the group consisting of radiofrequency, microwave and light. The patch may be implanted in the subject or topically positioned in relation to the subject, and controlled locally or remotely by an external controller, such as a microprocessor.

In another embodiment of the present invention, there is provided a system for controlling the rate of pharmaceutical delivery or biomolecule collection in a subject, comprising: a means to generate electromagnetic energy; a means to deliver the electromagnetic energy to the subject; and a means to administer the pharmaceutical to or collect the biomolecule from the subject, wherein the pharmaceutical is contained in a patch controlled locally or remotely by an external controller. Preferably, the electromagnetic energy is selected from the group consisting of radiofrequency, microwave and light, and means to generate electromagnetic energy include lasers and ultrasound transducers. Preferably, the controller is a microprocessor, powered by a battery, a solar cell, an electrochemical generator, a thermal energy generator, or an piezeoelectric generator. The patch may be implanted in the subject or topically positioned in relation to the subject, and furthermore, the patch may be made of material selected from the group consisting of a dressing material, a gel, a viscous material, and an adhesive material.

In a preferred embodiment, the patch contains one or more reservoirs separated by a rupturable membrane(s). In the case of multiple reservoir-containing patch, lyophilized crystal portion of an unstable pharmaceutical compound is stored in one reservoir, while liquid portion of the compound is stored in another reservoir. An example of such compound is prostaglandin E1.

The above disclosed system can further comprise an electrode, wherein the electrode is in contact with both the patch and controller, and transmits an electrical current or electromagnetic radiant energy. Or the same system can further comprises a computer monitor connected to the Internet, wherein a signal is sent over the Internet, through the computer monitor, and into the patch.

In still another embodiment of the present invention, there is provided a drug delivery or biomolecule collection patch, wherein the patch is electronically monitored by global positioning system.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIG. 1 shows a transdermal patch with electromagnetic energy controller 10, electrode 20 for transmitting energy, drug reservoir 30 containing the formulation and adhesive backing 40 for attachment to skin.

DETAILED DESCRIPTION OF THE INVENTION

The present invention provides methods/devices for remote and local controlled delivery of pharmaceutical compounds using electromagnetic energy. Electromagnetic devices described herein, including laser systems, are used to effect drug delivery and may be controlled locally or remotely by microprocessors integrated into the devices, which are in turn programmed to receive or transmit data over telecommunication networks. Controlled electromagnetic energy driven systems may be integrated into patches and other delivery devices that may be worn on the skin, or may be implanted.

The presently disclosed devices contain microprocessors or other electronically controlled elements that can be interrogated remotely or locally using integrated or remote transmitters. The transmitters in turn may be communicated with via telecommunication networks. Equipment used in paging systems is built into a transdermal patch that receives a signal, or code, sent by the operator over telecommunication networks. Control may also be exerted by coding systems, including bar and magnetic coding, communicated by devices that generate and read such code. Code may also be communicated via the Internet, either directly in the case of visible code, or through the use of dedicated communications devices that receive and process code.

In one embodiment of the present invention, there is provided a method for controlling delivery of a pharmaceutical compound in a subject, comprising the steps of: irradiating the subject with electromagnetic energy; and applying the pharmaceutical compound to the subject, wherein the compound is contained in a patch. Preferably, the electromagnetic energy is selected from the group consisting of radiofrequency, microwave and light. Still preferably, the patch is implanted in the subject or topically positioned in relation to the subject, and controlled locally or remotely by an external controller, such as a microprocessor.

In a preferred embodiment, the patch is made of material selected from the group consisting of a dressing material, a gel, a viscous material, and an adhesive material.

In another preferred embodiment, the pharmaceutical compound is selected from the group consisting of an anesthetic drug, an anti-neoplastic drug, a photodynamic therapeutical drug, an anti-infection drug, and an anti-inflammatory drug. More preferably, the anesthetic drug is lidocaine.

In another embodiment of the present invention, there is provided a system for controlling the rate of pharmaceutical delivery or biomolecule collection in a subject, comprising: a means to generate electromagnetic energy; a means to deliver the electromagnetic energy to the subject; and a means to administer the pharmaceutical to or collect the biomolecule from the subject, wherein the pharmaceutical is contained in a patch controlled locally or remotely by an external controller. Preferably, the electromagnetic energy is selected from the group consisting of radiofrequency, microwave and light, and means to generate electromagnetic energy include lasers and ultrasound transducers. Still preferably, the controller is a microprocessor, powered by a battery, a solar cell, an electrochemical generator, a thermal energy generator, or an piezeoelectric generator. Yet still preferably, the patch is implanted in the subject or topically positioned in relation to the subject, and made of material selected from the group consisting of a dressing material, a gel, a viscous material, and an adhesive material.

In a preferred embodiment, the patch contains one or more reservoirs separated by a rupturable membrane(s). In the case of multiple reservoir-containing patch, lyophilized crystal portion of an unstable pharmaceutical compound is stored in one reservoir, while liquid portion of the compound is stored in another reservoir. An example of such compound is prostaglandin E1.

The above disclosed system can further comprise an electrode, wherein the electrode is in contact with both the patch an d controller, and transmits an electrical current or electromagnetic radiant energy. Or the same system can further comprises a computer monitor connected to the Internet, wherein a signal is sent over the Internet, through the computer monitor, and into the patch.

In still another embodiment of the present invention, there is provided a drug delivery or biomolecule collection patch, wherein the patch is electronically monitored by global positioning system. Preferably, the global positioning system is a global positioning satellite receiver.

The following examples are given for the purpose of illustrating various embodiments of the invention and are not meant to limit the present invention in any fashion.

EXAMPLE 1

Pressure Waves for Driving Compounds Through Skin or Membranes

Pressure waves created through the interaction of electromagnetic energy with tissue or non-biological matter may be used to drive molecules in a medium across tissue interfaces or between cellular junctions such as those found in membranes, between cells, or even through cellular membranes. The interaction of radiofrequency or microwave irradiation with tissue or another absorber and various pharmaceutical formulations can lead to the generation of propagating pressure waves (generated from a rapid volumetric change in the medium by heating, or by the generation of plasma) which are in the form of low pressure acoustic waves propagating at the speed of sound or high pressure shock waves propagating at supersonic speeds. These waves can also be a consequence of a generation of waves in a non-biological target which is in intimate acoustic contact with the biological media. Continuously pulsing electromagnetic energy delivered in discrete short duration pulses propagates the pressure waves which thereby physically move the molecules between cellular junctions or across membranes. The "pumping" effect may occur through the creation of increased pressure, including osmotic or atmospheric pressure. A separation results, which is due to the differential resistance of the tissues or membranes relative to the fluid medium, which is the mobile phase. The degree of pumping will be related to the shape, duty cycle, and power of the driving RF.

Pumping may at times be inefficient if the energy is deposited directly on a tissue due to its large surface area. To compensate for this inefficiency, a target material which preferentially absorbs energy at these radiofrequency frequencies, may be placed adjacent to the tissue, in order to transfer energy effectively. This target could effectively act as an antenna and may optionally be composed of metals or metal containing compounds.

EXAMPLE 2

Pressure Waves for Altering the Barrier Function of Skin or Membranes

Pressure waves can be used to alter the skin or membrane itself thereby reducing its barrier function. This barrier function alteration will be transient; the integrity of the barrier function will reestablish itself soon after the radiofrequency energy ceases to impinge on the tissue. The degree to which the barrier function is reduced will be dependent on the frequency and intensity of the radiofrequency radiation. The pharmaceutical to be applied to the tissue is preferentially in place during irradiation.

EXAMPLE 3

Dipole Trapping

The force arising from a coherent interaction with light is also called the dipole force. A laser field polarizes the atom, and the polarized atom experiences a force in the gradient of an electromagnetic filed. The strong electric filed of a laser beam can be used to induce a dipole moment in a process called optical trapping. As long as the frequency of the laser field is below the natural resonance of the particle being trapped (e.g. below the atomic transition of an atom or the absorption edge of a polystyrene sphere), the dipole moment is in phase with the driving electrical field. Because the energy of the induced dipole p in the laser field E is given by $W=-pE$; the particle achieves a lower energy state by moving into the high-intensity focal spot of the laser beam. There have been numerous reports of optical traps being used to manipulate Particles, or even cells. These traps are used to move these tiny particle around under a microscope lens for manipulation. Optical tweezers have also been described whereby a focal spot of a single beam optical trap is moved with mirrors or lenses.

In the present study, a dipole is formed using radiofrequency or microwave energy, rather than laser energy. The trap is formed at the interface between molecules in a formulation and a tissue or membrane interface. This trap is then moved vectorially in the desired direction of movement. In the case of drug delivery, the desired direction is into the tissues. Thus, the focal point of the trap is moved along a vector that penetrates the tissue of interest, while a formulation containing the drug is applied to the surface of the tissue. The focal point of a single beam or multiple beam trap would then be moved progressively into the tissue, which could occur cyclically so as to ensure the maximum pumping effect.

EXAMPLE 4

Creation of Pores in Skin or Membranes

Small pores are made in the skin or membrane by applying the electromagnetic energy with needle-like probes. For example, a patch-like device with thousands of tiny, needle-like probes which conduct electomagnetic energy can deliver the energy to create pores. These probes can be made of silicon with a metallic conducting material.

EXAMPLE 5

Ablation or Alteration of Membranes and Tissues

Radiofrequency or microwave energy is applied directly to the surface of the tissue, or to a target adjacent to the tissue, in such a way that the epithelial layers of the tissue are altered to make the layers "leaky" to substances such as pharmaceuticals. In the case of skin, the stratum corneum may be ablated through the application of electromagnetic energy to generate heat. Alternatively, shear forces may be created by targeting this energy on an absorber adjacent to the skin, which transfers energy to create stress waves that alter or ablate the stratum corneum. Specifically, radiofrequencies producing a desired rapid heating effect on stratum corneum result in an ablative event, while minimizing coagulation. The removal of the stratum corneum in this way will result in increased permeability of compounds across the compromised tissue interface. For example, application of 4% lidocaine to a section of skin with stratum corneum ablated in this way will result in a rapid (minutes to onset) anesthesthetic effect.

Alternatively, delivery of electromagnetic energy at these wavelengths may be optimized, by adjusting pulse duration, dwell time between pulses, and peak-power to result in a rapid, intermittent excitation of molecules in the tissues of interest, such that there is no net coagulation effect from heating, but molecules are altered transiently to effect a transient change in membrane conformation that results in greater "leakiness" to substances such as pharmaceuticals. Furthermore, energy with the appropriate pulse mode characteristics is continuously applied that these transient alterations are maintained during the energy cycle, thus creating a means for maintaining increased membrane permeability over time. This method allows substances to be continually delivered over a desired period of time.

EXAMPLE 6

Combinations of Techniques to Effect Molecular Delivery or Collection: Applying Pressure to Permeabilized Membranes A "leaky" membrane or ablation site in skin is created by first applying electromagnetic energy, including light, microwave or radiofrequency, such that membrane or intramembrane structures are realigned, or the membrane is compromised otherwise, so as to improve permeation. This step is followed by application of electromagnetic energy induced pressure to drive molecules across tissue interfaces and between cellular junctions at a greater rate than can be achieved by either method alone. The laser energy may be delivered continuously or in discrete pulses to prevent closure of the pore. Optionally, a different wavelength laser may be used in tandem to pump molecules through the pore than is used to create the pore. Alternatively, a single laser may be modulated such that pulse width and energy vary and alternate over time to alternately create a pore through which the subsequent pulse drives the molecule.

Alternatively, intact skin is treated such that the stratum corneum is; compromised leading to a decrease in resistance and increased permeability to molecules in general. This step is followed by application of a electromagnetic energy generated pressure wave to drive molecules across membranes and between cellular junctions at a greater rate than can be achieved by either method alone.

Laser energy is directed through optical fibers or guided through a series of optics such that pressure waves are generated to come in contact with or create a gradient across the membrane surface. These pressure waves may be optionally used to create a pressure gradient such that the pressure waves move through a liquid or semi-solid medium thereby "pumping" compounds through the medium, into and across the membrane.

This technology may optionally be used to deliver laser energy for the purpose of drug delivery across, for example, buccal, uterine, intestinal, urethral, vaginal, bladder and ocular membranes. Pharmaceutical compounds may be delivered into cellular spaces beyond these membranes or into chambers encompassed by these membranes. Compromised or intact stratum corneum may also be breached by, applying appropriate optical pressure.

EXAMPLE 7

Formulations

Specific formulations are chosen such that electromagnetic energy absorption is maximized relative to the surrounding medium. Further, many pharmaceutical or diagnostic compounds can be modified by the addition of such energy absorbing groups (or selecting those that minimize absorption) so as to maximize the effects of the electromagnetic energy on a particular formulation relative to the surrounding medium or tissue. A new class of compounds is therefore defined that have unique permeability and migration characteristics in the presence of, or following a treatment of electromagnetic energy as described here. These molecules possess different characteristics by virtue of the addition of, groups or structures that absorb energy in a characteristic way that may impart momentum to the molecule causing it to move relative to the medium which contains it, or may result in excitation of the molecule to result in a desired alteration of that molecule. For example, rapid heating of a molecule, which preferentially absorbs energy relative to its environment, by radiofrequency or microwave energy could result in cleavage of a heat-sensitive linkage or activation of a specific activity. These compounds are designed to include both physiologically active groups and molecular groups which maximize the absorbance or reflectance of energy to achieve the desired effect. In these examples, an analogy is drawn to photodynamic therapy whereby molecules absorb photons and make interstate transition from ground to excited singlet state whereupon they transfer energy to ground sate oxygen thus exciting it to a excited singlet state which is toxic.

Similarly, pharmaceutically active compounds may be modified by the addition of groups that readily form a dipole when exposed to appropriate electromagnetic energy, such as radiofrequencies or microwaves. The addition of such groups would result in enhanced ability to use optical trapping methods for the delivery of these types of compounds as described herein. Further, any compound which may interact with electromagnetic energy in such a way that it is propelled through a medium can be used. Thus, the present study defines a means by which molecules may be propelled through a medium at differential rates relative to the medium and other molecules in the medium, and a means by which molecules may be separated from one another based on their optical characteristics.

The application is not limited to delivering pharmaceuticals. Other separations of molecules may be achieved by the methods described herein, such as separating protein species in polyacrylamide gels, or separating oligonucleotides on microarray devices. These examples also include using magnetic fields alone to propel molecules through a medium or tissue based on intrinsic magnetic properties or by the addition of magnetic groups, metals, etc. Such methods may also be enhanced by using them in combination with methods to alter membranes and tissues to work synergistically.

Thermal or electronic disruption of a molecule may be a problem, however, appropriate carriers may be selected to solve this problem. The carriers selected act as "sinks" for the energy, while functional groups are selected that are stable. Attaching these "sinks" to functional groups results in the energy being absorbed preferentially to the sink, thereby limiting exposure to the functional groups. Alternatively, molecules may be developed that have functional groups attached to a backbone molecule that is susceptible to cleavage when exposed to electromagnetic energy described herein. Specifically, radiofrequency waves may result in excess vibration of groups as they absorb the energy. Using a linker that is susceptible to cleavage when its atoms vibrate in this way will result in the release of the functional group of interest, which could be a pharmaceutically active substance.

EXAMPLE 8

Transdermal Patches

Patches, such as transdermal drug delivery patches, are controlled by remote or local operation through microprocessors. Such patches are designed and used together with electromagnetic energy driven delivery systems.

Patches used herein include a dressing material which contains a gel or adhesive that in turn contains the drug formulation to be delivered. The dressing is in contact with an electrode, which is, in turn, in contact with the controller (see FIG. 1). The controller regulates the flow of electromagnetic energy that contacts the electrode. The electrode distributes the energy to the formulation, and further into the tissue of interest. Besides a dressing, the, patch may be a gel, viscous material, or other patch material that covers the site of treatment.

The patch may contain one or more reservoirs. In the case of multiple reservoirs, a rupturable membrane may separate different chambers, thus preventing mixing of components until the membrane is ruptured. In the case of an unstable compound such a s prostaglandin E1 (e.g. Caverject, UpJohn), lyophilized crystals could be stored in one reservoir while the liquid components to be mixed with the drug could be stored in another reservoir. The two reservoirs are separated by a membrane that may be ruptured by crushing or other physical means, thereby allowing the components to mix freely to make available for dosing. This multi-reservoir concept may be further extended to include mixing of chemicals that will generate: an electrical current, for the purpose of iontophoresis or electroporation.

Healing at the site of ablation will ultimately reduce the amount of drug that permeates over time. A substance may be included in the drug formulation or patch and applied to the site of permeation/ablation whereby this substance slows the healing process or reduces the rate of scab formation thereby limiting the rate of closure of the permeation site and having the effect of extending the enhanced permeability characteristics of the irradiated site.

EXAMPLE 9

Communication Systems

The controller may be comprised of a current generator driven by a transportable battery, a solar powered generator, an electrochemical generator, a thermal energy generator, a piezoelectric generator, a radiofrequency generator, a microwave generator, etc. The electrode of the patch may be replaced by a laser, multiple lasers, or optical fibers which conduct and transmit light at a desired wavelength, pulse length, pulse energy, pulse number and pulse repetition rate to ablate or alter the tissue directly beneath the patch. Alternatively, continuous wave lasers may be used to effect alterations in the tissues that would lead to a permeabilizing effect. Lasers and other electromagnetic energy generators, as well as ultrasound transducers, may be used in controller-electrode combinations that will result in the desired effects. Also inherent in the design of these patches is the ability to deliver the drugs simultaneously with the energy, or at any time before or after energy administration.

Telecommunication networks transmit data between the operator and the remotely sited controller (on the patch). The device includes a telemetry transceiver for communicating data and operating instructions between the device and an external patient communications control device that is either worn by, located in proximity to the patient, or at a remote location within the device transceiving range. The control device preferably includes a communication link with a remote medical support network through telecommunication network(s) and may include a global positioning satellite receiver for receiving positioning data identifying the global position of the control device.

The device may also contain a patient activated link for permitting patient initiated personal communication with the medical support network. A system controller in the control device controls data and digital communications for selectively transmitting patient initiated personal communications and global positioning data to the medical support network, for receiving telemetry out of data and operating commands from the medical support network, and for receiving and initiating re-programming of the device operating modes and parameters in response to instructions received from the medical support network. The communication link between the medical support network and the patient communications control device may comprise a world wide satellite network, hard-wired telephone network, a cellular telephone network or other personal communication system.

An objective of the device is to provide the patient greater mobility. The patient is allowed to be ambulatory while his medical condition is monitored and/or treated by the medical device. Programming devices may be controlled by the physician or pharmacy, and code or data transmitted over telecommunication networks to the site of the device. This can happen remotely or locally. Currently, telemetry systems used to communicate with medical devices are positioned within a short distance of the device. Furthermore, transdermal patch systems are currently regulated only by passive controls, built into the patch, which regulate the dosage. These controls are typically not electronic, but rather based on membrane and diffusion characteristics of the patch and formulation. The present device provides a means for a remote operator to adjust the dosage and timing of drug delivery, while the patient is ambulatory.

Another object of the device is to provide a patient data communication system for world wide patient re-programming telemetry with a medical device worn by the patient. The device described herein is a transdermally worn patch containing a drug formulation which may or may not include electromagnetic energy permeation enhancement. However, the invention is not limited to transdermal drug delivery and may include communication with implanted drug delivery devices using the aforementioned electromagnetic energy based delivery technology.

The presently disclosed device transmits and receives coded information from a remote or local source. The operator at the, device is positioned at a location, and can transmit information from the medical support network. The device incorporates a wireless interface including a control device telemetry transceiver for receiving and transmitting coded communications between the system controller and the device telemetry transceiver, a global positioning system coupled to the system controller for providing positioning data identifying the global position of the patient to the system controller; communication means for communicating with the remote medical support network; and communication network interface means coupled to the system controller and the communication means for selectively enabling the communication means for transmitting the positioning data to the medical support network and for selectively receiving commands from the medical support network. The communication interface may include capabilities for transfer of data between the patient and the operator by cellular telephone network, paging networks, satellite communication network, land-based telephone communication system, or modem-based communication network, including the Internet. Communications may include but not be limited to microwave, radiofrequency and digital communication via optical means.

The communication and monitoring systems provide a means for exchanging information with and exercising control over one or more medical devices attached to the body of a patient. The devices are intended to function no matter how geographically remote the patient may be relative to the monitoring site or medical support network. The operator, usually a physician, types in a code, which is transmitted over the medical support network to the patient, who may be located by a geopositioning satellite or in relation to other telecommunication network. The code contains information which activates the device and controls dosage.

Data transmission to and from the operator to the device is accomplished by means of a control device that transmits data over the communication network. A telemetry antenna and associated transmitter/receiver can both download and upload data. The antenna may function on radiofrequencies. Control of dosage in the device itself is provided by a digital controller/timer circuit with associated logic circuits connected with a microcomputer. The microcomputer controls the operational functions of a digital controller and a timer. It specifies activation, timing and duration of events. The microcomputer contains a microprocessor and associated RAM and ROM chips, depending on the need for additional memory and programmable functions.

A base station may exist at the operator's location. The base station may be comprised of a microprocessor-controlled computer with hardware and software, and associated modem for transmission of information that is relayed through the appropriate communication network. The system controller may also be coupled to a GPS receiver for receiving positioning data from an earth satellite. The GPS receiver may use currently available systems.

EXAMPLE 10

Bar-coded Prescriptions

Dosage schedules for certain medications can be pre-encoded by the manufacturer or pharmacy, using bar code symbols. The encoded bar code symbols can be compiled on one or more menu sheets accessible at the physician office or pharmacy counter where the controller is installed. In such applications, a bar code symbol reading device can be linked to a data communication port of the medical support network and located on the patch, which can then be used to program the proper dosage into the device. The code could be transmitted over the Internet, or via other telecommunication networks into a device in the possession of the patient, who can then read the bar code into the patch.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A system for controlling and increasing the rate of delivery of a pharmaceutical to a subject, comprising:

a patch topically positioned in relation to said subject, said patch comprising:

said pharmaceutical;

an electrode in direct contact with the patch, said electrode transmitting radiofrequency energy or microwave energy into the patch thereby distributing said radiofrequency or microwave energy to said pharmaceutical, to said subject or to both said pharmaceutical and said subject, wherein said radiofrequency energy or said microwave energy creates a pressure wave to propel said pharmaceutical through one or more tissues in said subject or alters permeability of said tissue(s) to said pharmaceutical in said subject or, in combination, propels said pharmaceutical across said altered tissues, a microprocessor, said microprocessor positioned externally to the patch but in contact with said electrode such that said electrode is in direct contact with both the patch and a controller in said microprocessor, said controller regulating transmission of said radiofrequency or microwave energy through said electrode via local transmission or via remote transmission of a signal to said microprocessor; and a communication means to monitor and/or to interrogate said microprocessor, further comprising a means to transmit said signal to said microprocessor;

wherein integration of said electrode and of said microprocessor into the patch provides controlled and increased rate of drug delivery to the subject wearing the patch while the subject is ambulatory and, optionally, geographically remote from the communication means.

2. The system of claim 1, wherein said microprocessor is powered by a radiofrequency generator or a microwave generator.

3. The system of claim 1, wherein said patch is made of a dressing material, a gel, a viscous material, or an adhesive material.

4. The system of claim 1, wherein said patch contains one or more reservoirs separated by at least one rupturable membrane.

5. The system of claim 4, wherein the multiple reservoir-containing patch stores an unstable pharmaceutical compound, wherein a lyophilized crystal portion of said compound is stored in a first reservoir and a liquid portion of said compound is stored in a second reservoir.

6. The system of claim 5, wherein said pharmaceutical compound is prostaglandin E1.

7. The system of claim 1, wherein said communication means comprises a computer monitor connected to the Internet.

8. The system of claim 1, wherein said communication means monitors the geographical location of the subject wearing the patch via a global positioning system.

9. The system of claim 8, wherein said global positioning system is a global positioning satellite receiver.

10. The system of claim 1, wherein said pharmaceutical compound is selected from the group consisting of an anesthetic drug, an anti-neoplastic drug, a photodynamic therapeutical drug, an anti-infection drug, and an anti-inflammatory drug.

11. The system of claim 10, wherein said anesthetic drug is lidocaine.

* * * * *